(12) United States Patent
Leonetti et al.

(10) Patent No.: US 9,068,161 B2
(45) Date of Patent: Jun. 30, 2015

(54) LACCASES AND USES THEREOF

(75) Inventors: Jean-Paul Leonetti, Castelnau-le-Lez (FR); Jean-Michel Claverie, Cassis (FR); Nicolas Chabot, Montpellier (FR)

(73) Assignee: DEINOVE, Grabels (FR)

( * ) Notice: Subject to any disclaimer, the term of this patent is extended or adjusted under 35 U.S.C. 154(b) by 0 days.

(21) Appl. No.: 13/884,103

(22) PCT Filed: Nov. 8, 2011

(86) PCT No.: PCT/EP2011/069670
§ 371 (c)(1),
(2), (4) Date: Aug. 1, 2013

(87) PCT Pub. No.: WO2012/062768
PCT Pub. Date: May 18, 2012

(65) Prior Publication Data
US 2013/0309730 A1   Nov. 21, 2013

Related U.S. Application Data

(60) Provisional application No. 61/411,182, filed on Nov. 8, 2010.

(51) Int. Cl.
*C12N 9/02* (2006.01)
*C12N 1/22* (2006.01)
*C12P 7/10* (2006.01)

(52) U.S. Cl.
CPC ............... *C12N 9/0061* (2013.01); *C12N 1/22* (2013.01); *C12P 7/10* (2013.01); *Y02E 50/16* (2013.01)

(58) Field of Classification Search
None
See application file for complete search history.

(56) References Cited

FOREIGN PATENT DOCUMENTS

| JP | 2009 017796 | 1/2009 |
|---|---|---|
| WO | WO 2009/063079 | 5/2009 |
| WO | WO 2009/149027 | 12/2009 |
| WO | WO 2010/006228 | 1/2010 |
| WO | WO 2010/042842 | 4/2010 |

OTHER PUBLICATIONS

Database Accession No. AWC86649, "Thermus thermophiles laccase protein, SEQ ID 1." Apr. 2, 2009, p. 1, XP-002666105.
Miyazaki, K. "A hyperthermophilic laccase from *Thermus thermophilus* HB27" *Extremophiles*, 2005, pp. 415-425, vol. 9.
Dwivedi, U. N. et al. "Structure-function relationship among bacterial, fungal an dplant laccases" *Journal of Molecular Catalysis B: Enzymatic*, 2011, pp. 117-128, vol. 68.

*Primary Examiner* — Suzanne M Noakes
(74) *Attorney, Agent, or Firm* — Saliwanchik, Lloyd & Eisenschenk

(57) ABSTRACT

The present invention relates to novel enzymes and the uses thereof. The invention also relates to methods of producing such enzymes, coding nucleic acid molecules, recombinant cells and methods of modifying biomass from such materials. The invention is particularly suited to degrade biomass and/or to improve biomass degradation. The invention also relates to various applications of the enzymes of the invention for the production of bioenergy (such as bioethanol), as well as in the field of chemistry, paper industry, textile industry and beverage industry.

18 Claims, No Drawings

SEQUENCE LISTING

<160> NUMBER OF SEQ ID NOS: 9

<210> SEQ ID NO 1
<211> LENGTH: 1446
<212> TYPE: DNA
<213> ORGANISM: Deinococcus sp.
<220> FEATURE:
<221> NAME/KEY: misc_feature
<223> OTHER INFORMATION: Laccase 1 derived from Deinococcus cellulolyticus DRH46

<400> SEQUENCE: 1

```
atgaaacaga ggctcactgc agcagccctg ctgactgccc tgttgtccag ttgtgccatg      60
aaaaacccgg atgtcatttc gtatcaggac cctgagccac tggcaggcca gcgcagtggc     120
aaagctgccg aattcaccct caccgcgcag aaaagccgtc tggaccttgc aggccagtcg     180
gtggaggccc tgacctacaa cggcacgttc ccgggtcctc tgctgaccct gaaagccgga     240
gaggacgtgc ggatcaccct caaaaacaac ctctccgagc ccaccaacct gcacctgcac     300
ggactccccc tctctccaga ggtggatgat cctttttgtgg tggtccctcc cgggggatct     360
cacacctacg ctttccaggt gcctgaagag gtgcatggca ccttctggta tcacacccac     420
acccacgggg cttctgcagc acaactgttt tcaggcctgg caggaccact gttggtggag     480
gcagcaaagc cgaacaaccc cattgagcac atggagaccc acacggtggt cttcaaggac     540
ctgccaggtg cgcagcacgc agacgacggt gtcctgatga acgacgtga aaacaccctg     600 ctggtcaatg gccttgtctc tcccactttg aagaccgaaa acagctgggt gcagctccgc     660
ctgatcaatg cctccaatgc ccgttacctg cgcctgaaac tggatgatgg cctcttgcag     720
gtggtggccc gtgacggcat cgaccttcca ggcatggaac gggcacagga actgctgctg     780 accccggcg agcgggcaga tgtgctggtc tccttgcagg accaccagaa cctcaaactg     840
cagaacctgc cttacgaccg tggcgtgcac agcatgggga gccattcggg ccacacggag     900
agcaagacag ctgtggtcct gaccctgcag gggccacaga aacctggagc cagcgttccc     960
cgcgttgaaa ctgcacctcc acccttttta caactgcagg gcaatgaaaa agtgcggaaa    1020
gtgatcctgc aggaaaccat gcagcccgtg aagttcttca tcaacggacg cagcttcgac    1080
atgaaccggg tggattttca tgtctccgag ggcagcaccg aaatctggga attgcagaac    1140
```

```
accaccgaaa tggaccaccc tttccacctc cacaccttcc caatgcagct gattcgcatc    1200
ggtggcaagg aggtccctcc ggtctggaag gacaccgtga acatcccgaa aaacagcacc    1260
gtcactgtgg ccgtgcactt caaaggcttc acgggcaaga ccgttttcca ctgtcacatc    1320
gccgagcatg aagaagccgg gatgatgggt cttcttcagg tgcatccctc tgggacagca    1380
ctcccggcct ctctggagcc cattgaaccc acagtgggtc caggagaaga cgcacaacac    1440
gggcac                                                              1446
```

<210> SEQ ID NO 2
<211> LENGTH: 482
<212> TYPE: PRT
<213> ORGANISM: Deinococcus sp.
<220> FEATURE:
<221> NAME/KEY: MISC_FEATURE
<223> OTHER INFORMATION: Laccase 1 derived from Deinococcus cellulolyticus DRH46

<400> SEQUENCE: 2

```
Met Lys Gln Arg Leu Thr Ala Ala Leu Leu Thr Ala Leu Leu Ser
1               5                   10                  15

Ser Cys Ala Met Lys Asn Pro Asp Val Ile Ser Tyr Gln Asp Pro Glu
                20                  25                  30

Pro Leu Ala Gly Gln Arg Ser Gly Lys Ala Ala Glu Phe Thr Leu Thr
            35                  40                  45

Ala Gln Lys Ser Arg Leu Asp Leu Ala Gly Gln Ser Val Glu Ala Leu
        50                  55                  60

Thr Tyr Asn Gly Thr Phe Pro Gly Pro Leu Thr Leu Lys Ala Gly
65                  70                  75                  80

Glu Asp Val Arg Ile Thr Leu Lys Asn Asn Leu Ser Glu Pro Thr Asn
                85                  90                  95

Leu His Leu His Gly Leu Pro Leu Ser Pro Glu Val Asp Asp Pro Phe
            100                 105                 110

Val Val Val Pro Pro Gly Gly Ser His Thr Tyr Ala Phe Gln Val Pro
        115                 120                 125

Glu Glu Val His Gly Thr Phe Trp Tyr His Thr His Thr His Gly Ala
    130                 135                 140

Ser Ala Ala Gln Leu Phe Ser Gly Leu Ala Gly Pro Leu Leu Val Glu
145                 150                 155                 160

Ala Ala Lys Pro Asn Asn Pro Ile Glu His Met Glu Thr His Thr Val
                165                 170                 175

Val Phe Lys Asp Leu Pro Gly Ala Gln His Ala Asp Asp Gly Val Leu
            180                 185                 190

Met Asn Gly Arg Glu Asn Thr Leu Leu Val Asn Gly Leu Val Ser Pro
        195                 200                 205

Thr Leu Lys Thr Glu Asn Ser Trp Val Gln Leu Arg Leu Ile Asn Ala
    210                 215                 220

Ser Asn Ala Arg Tyr Leu Arg Leu Lys Leu Asp Asp Gly Leu Leu Gln
225                 230                 235                 240

Val Val Ala Arg Asp Gly Ile Asp Leu Pro Gly Met Glu Arg Ala Gln
                245                 250                 255

Glu Leu Leu Leu Thr Pro Gly Glu Arg Ala Asp Val Leu Val Ser Leu
            260                 265                 270

Gln Asp His Gln Asn Leu Lys Leu Gln Asn Leu Pro Tyr Asp Arg Gly
        275                 280                 285
```

```
Val His Ser Met Gly Ser His Ser Gly His Thr Glu Ser Lys Thr Ala
    290                 295                 300

Val Val Leu Thr Leu Gln Gly Pro Gln Lys Pro Gly Ala Ser Val Pro
305                 310                 315                 320

Arg Val Glu Thr Ala Pro Pro Pro Phe Leu Gln Leu Gln Gly Asn Glu
                325                 330                 335

Lys Val Arg Lys Val Ile Leu Gln Glu Thr Met Gln Pro Val Lys Phe
                340                 345                 350

Phe Ile Asn Gly Arg Ser Phe Asp Met Asn Arg Val Asp Phe His Val
                355                 360                 365

Ser Glu Gly Ser Thr Glu Ile Trp Glu Leu Gln Asn Thr Thr Glu Met
    370                 375                 380

Asp His Pro Phe His Leu His Thr Phe Pro Met Gln Leu Ile Arg Ile
385                 390                 395                 400

Gly Gly Lys Glu Val Pro Pro Val Trp Lys Asp Thr Val Asn Ile Pro
                405                 410                 415

Lys Asn Ser Thr Val Thr Val Ala Val His Phe Lys Gly Phe Thr Gly
                420                 425                 430

Lys Thr Val Phe His Cys His Ile Ala Glu His Glu Glu Ala Gly Met
                435                 440                 445

Met Gly Leu Leu Gln Val His Pro Ser Gly Thr Ala Leu Pro Ala Ser
    450                 455                 460

Leu Glu Pro Ile Glu Pro Thr Val Gly Pro Gly Glu Asp Ala Gln His
465                 470                 475                 480

Gly His

<210> SEQ ID NO 3
<211> LENGTH: 1476
<212> TYPE: DNA
<213> ORGANISM: Deinococcus sp.
<220> FEATURE:
<221> NAME/KEY: misc_feature
<223> OTHER INFORMATION: Laccase 2 derived from Deinococcus
      cellulolyticus DRH46

<400> SEQUENCE: 3
atgattcgaa ccctcacttc cctcaccctg ctgaccgtgg cgctcaccgc atgcgctcca      60
aaaggaagtc ccatgaccga gtaccacaac cctgctgaag tgcaagcaag ccgcacagaa     120
aaaggcagca ccttcaccct caccgccgca gaaaccagca tcaccctgga cggcaaagag     180
gtgaaagcac agctcttcaa ccagagtttt cccggacccc agctcaccct gcaggccgga     240
gaacaggtga acctcaccct caaaaacgac ctccgtgaac ccaccaacct gcacctgcac     300
ggcctgaccc tcccggcagg ggtggacgat cccttctgc aggtccagcc cggagaaagc      360
cacacctaca gcttcactgt ccgcaaggc ctgcacggca ccttctggta ccacacccac      420
acccatgggc acctcggaac acaactcttc cagggcctcg caggacccct gatcgtcgag     480
gaccccacct ttgacagcca catccagggg atggagaccc acaccgtggt gctcaaagac     540
ctccctgttg aagtacagga cagtgacggc acccgcatga cggccgggaa aggcaaactg     600
ctggtcaacg gcctctcctc ccccaccctg aagaccgaaa gcagctgggt gaggctccgc     660
ctgatcaacg cttcaaacgc ccgctatgac ctgctgaaac tctctggttc agcttttctc     720
cacgtcatcg ccaaggacgg gatcgacctg cccaaaaacg agcaggtgaa agaactcctc     780
ctcacccccg cgagcgggc cgatgtgctg atttccgtgc aagaccagca ggacctccgg     840
ctggaaaacc accctttacga ccggggggtg catgagatgg acgggggggca tcagggtcac    900
```

```
acacccagca caccagaggt gctcctcacc ctgcagggga agaaagggag cgtctcagcc    960
agcgtgccac aacctgccct gcagccccgt ccattcctga aggtgactgg caacgaagcc   1020
attcgcaagg tggtgctgca agaaaccatg cagcctgtga aattcttcat caacggacgc   1080
acgtttgaca tgaaccgggt ggatttccat gtctctgaag caccaccga aatctgggag    1140 gtggagaacc agaccgaaat ggaccacccc ttccacctgc acacttccc ggtgcaggtc    1200 ctctcggtga acggccagga agtgcctccg gtgtggaagg acaccgtgaa cgtccctgcg   1260
aaagcaaaag tgcaggtggc cgtgaaattt gagggcttca ccggcaagac ggtcttccac   1320
tgccacattg ccgagcacga agaagagggc atgatgggcg tcttgcaggt gcatccagca   1380
ggtgaggcgc tccctgcgtc tctcacaccc acccttcccc ctgcagctgc ttcggaggac   1440
atgcctgaca tgcccggcat ggaccacagt ggccac                             1476
```

<210> SEQ ID NO 4
<211> LENGTH: 492
<212> TYPE: PRT
<213> ORGANISM: Deinococcus sp.
<220> FEATURE:
<221> NAME/KEY: MISC_FEATURE
<223> OTHER INFORMATION: Laccase 2 derived from Deinococcus
     cellulolyticus DRH46

<400> SEQUENCE: 4

```
Met Ile Arg Thr Leu Thr Ser Leu Thr Leu Leu Thr Val Ala Leu Thr
1               5                   10                  15

Ala Cys Ala Pro Lys Gly Ser Pro Met Thr Glu Tyr His Asn Pro Ala
            20                  25                  30

Glu Val Gln Ala Ser Arg Thr Glu Lys Gly Ser Thr Phe Thr Leu Thr
        35                  40                  45

Ala Ala Glu Thr Ser Ile Thr Leu Asp Gly Lys Glu Val Lys Ala Gln
    50                  55                  60

Leu Phe Asn Gln Ser Phe Pro Gly Pro Gln Leu Thr Leu Gln Ala Gly
65                  70                  75                  80

Glu Gln Val Asn Leu Thr Leu Lys Asn Asp Leu Arg Glu Pro Thr Asn
                85                  90                  95

Leu His Leu His Gly Leu Thr Leu Pro Ala Gly Val Asp Asp Pro Phe
            100                 105                 110

Leu Gln Val Gln Pro Gly Glu Ser His Thr Tyr Ser Phe Thr Val Pro
        115                 120                 125

Gln Gly Leu His Gly Thr Phe Trp Tyr His Thr His Thr His Gly His
    130                 135                 140

Leu Gly Thr Gln Leu Phe Gln Gly Leu Ala Gly Pro Leu Ile Val Glu
145                 150                 155                 160

Asp Pro Thr Phe Asp Ser His Ile Gln Gly Met Glu Thr His Thr Val
                165                 170                 175

Val Leu Lys Asp Leu Pro Val Glu Val Gln Asp Ser Asp Gly Thr Arg
            180                 185                 190

Met Asn Gly Arg Glu Gly Lys Leu Leu Val Asn Gly Leu Ser Ser Pro
        195                 200                 205

Thr Leu Lys Thr Glu Ser Ser Trp Val Arg Leu Arg Leu Ile Asn Ala
    210                 215                 220

Ser Asn Ala Arg Tyr Asp Leu Leu Lys Leu Ser Gly Ser Ala Phe Leu
225                 230                 235                 240

His Val Ile Ala Lys Asp Gly Ile Asp Leu Pro Lys Thr Glu Gln Val
                245                 250                 255
```

Lys Glu Leu Leu Leu Thr Pro Gly Glu Arg Ala Asp Val Leu Ile Ser
            260                 265                 270

Val Gln Asp Gln Gln Asp Leu Arg Leu Glu Asn His Pro Tyr Asp Arg
        275                 280                 285

Gly Val His Glu Met Asp Gly Gly His Gln Gly His Thr Pro Ser Thr
    290                 295                 300

Pro Glu Val Leu Leu Thr Leu Gln Gly Lys Lys Gly Ser Val Ser Ala
305                 310                 315                 320

Ser Val Pro Gln Pro Ala Leu Gln Pro Arg Pro Phe Leu Lys Val Thr
                325                 330                 335

Gly Asn Glu Ala Ile Arg Lys Val Val Leu Gln Glu Thr Met Gln Pro
            340                 345                 350

Val Lys Phe Phe Ile Asn Gly Arg Thr Phe Asp Met Asn Arg Val Asp
        355                 360                 365

Phe His Val Ser Glu Gly Thr Thr Glu Ile Trp Glu Val Glu Asn Gln
    370                 375                 380

Thr Glu Met Asp His Pro Phe His Leu His Thr Phe Pro Val Gln Val
385                 390                 395                 400

Leu Ser Val Asn Gly Gln Glu Val Pro Pro Val Trp Lys Asp Thr Val
                405                 410                 415

Asn Val Pro Ala Lys Ala Lys Val Gln Val Ala Val Lys Phe Glu Gly
            420                 425                 430

Phe Thr Gly Lys Thr Val Phe His Cys His Ile Ala Glu His Glu Glu
        435                 440                 445

Glu Gly Met Met Gly Val Leu Gln Val His Pro Ala Gly Glu Ala Leu
    450                 455                 460

Pro Ala Ser Leu Thr Pro Thr Leu Pro Pro Ala Ala Ala Ser Glu Asp
465                 470                 475                 480

Met Pro Asp Met Pro Gly Met Asp His Ser Gly His
                485                 490

<210> SEQ ID NO 5
<211> LENGTH: 814
<212> TYPE: DNA
<213> ORGANISM: Deinococcus sp.
<220> FEATURE:
<221> NAME/KEY: misc_feature
<223> OTHER INFORMATION: Laccase 3 derived from Deinococcus maricopensis
      DSM 21211

<400> SEQUENCE: 5
atgacgctcc atactgacct gatgctgctg cgctccccgc acctcacgtt cccgcacgcg      60
ttctcgacgc gggcgggcgg cgtctcgagt ggcccgtacg cgggcctgaa cctcgacgac     120
cgcgaggacg acgcgcacag cgtcgccgag aaccgccgcc gcctcaccac gcagctcggg     180
ttcacgcccg cacgcgtagc gagcctcaca caggtccacg gcgcggacgt cgccgtggcg     240
agcgcgcccg gcgtgcacag cggtgacgcc atcgtcaccg cccagccgga cctgctgctc     300
gccatcatga cggccgactg ctacccgctg ctccttgagg acgccgaggc cggcgtgatc     360
ggcgcggcgc acgccggatg gcgcggcacg gtcgcccgca tcggcgcgcg caccattgag     420
gccatgaccc cgctgggcgc ccggccggaa cgcatccgcg ccgcggtcgg ccccggcatc     480
tgtggcgcgc ggtacgccgt cggcgaggac gtcgccgcgc agttccgcgc gcgggcctc      540 ggggacgcgc tgagcgggct gcagctggac ctcgcgcggg cgaacacaca ggtgctcgtc     600
gacgcgggcg tctccgcgtc gcacctgtgg ggtgtcgggg cgctgcacca cgaaccggac     660

```
ttctactcgt accgacggga tgccggacgc accgggcgga tgtgggccct gatcggccgc      720
ggaggcgcag aacctcacgg tgtgcgccgc gcgcccgacc ctaaaatggt gggtgctttg      780
gacacccaca cctctgccgg ggagggccgc gcgc                                  814
```

<210> SEQ ID NO 6
<211> LENGTH: 271
<212> TYPE: PRT
<213> ORGANISM: Deinococcus sp.
<220> FEATURE:
<221> NAME/KEY: MISC_FEATURE
<223> OTHER INFORMATION: Laccase 3 derived from Deinococcus maricopensis DSM 21211

<400> SEQUENCE: 6

```
Met Thr Leu His Thr Asp Leu Met Leu Leu Arg Ser Pro His Leu Thr
1               5                   10                  15

Phe Pro His Ala Phe Ser Thr Arg Ala Gly Gly Val Ser Ser Gly Pro
            20                  25                  30

Tyr Ala Gly Leu Asn Leu Asp Asp Arg Glu Asp Ala His Ser Val
        35                  40                  45

Ala Glu Asn Arg Arg Arg Leu Thr Thr Gln Leu Gly Phe Thr Pro Ala
    50                  55                  60

Arg Val Ala Ser Leu Thr Gln Val His Gly Ala Asp Val Ala Val Ala
65                  70                  75                  80

Ser Ala Pro Gly Val His Ser Gly Asp Ala Ile Val Thr Ala Gln Pro
                85                  90                  95

Asp Leu Leu Leu Ala Ile Met Thr Ala Asp Cys Tyr Pro Leu Leu Leu
            100                 105                 110

Glu Asp Ala Glu Ala Gly Val Ile Gly Ala Ala His Ala Gly Trp Arg
        115                 120                 125

Gly Thr Val Ala Arg Ile Gly Ala Arg Thr Ile Glu Ala Met Thr Arg
    130                 135                 140

Leu Gly Ala Arg Pro Glu Arg Ile Arg Ala Ala Val Gly Pro Gly Ile
145                 150                 155                 160

Cys Gly Ala Arg Tyr Ala Val Gly Glu Asp Val Ala Ala Gln Phe Arg
                165                 170                 175

Ala Ala Gly Leu Gly Asp Ala Leu Ser Gly Leu Gln Leu Asp Leu Ala
            180                 185                 190

Arg Ala Asn Thr Gln Val Leu Val Asp Ala Gly Val Ser Ala Ser His
        195                 200                 205

Leu Trp Val Ser Gly Arg Cys Thr Thr Glu Pro Asp Phe Tyr Ser Tyr
    210                 215                 220

Arg Arg Asp Ala Gly Arg Thr Gly Arg Met Trp Ala Leu Ile Gly Arg
225                 230                 235                 240

Gly Gly Ala Glu Pro His Gly Val Arg Arg Ala Pro Asp Pro Lys Met
                245                 250                 255

Val Gly Ala Leu Asp Thr His Thr Ser Ala Gly Glu Gly Arg Ala
            260                 265                 270
```

<210> SEQ ID NO 7
<211> LENGTH: 21
<212> TYPE: DNA
<213> ORGANISM: Artificial
<220> FEATURE:
<223> OTHER INFORMATION: sequence encoding 6(His) tag -continued

```
<400> SEQUENCE: 7
catcatcacc atcaccatta a                                              21

<210> SEQ ID NO 8
<211> LENGTH: 23
<212> TYPE: DNA
<213> ORGANISM: Artificial
<220> FEATURE:
<223> OTHER INFORMATION: primer 16S rDNA

<400> SEQUENCE: 8
gttacccgga atcactgggc gta                                            23

<210> SEQ ID NO 9
<211> LENGTH: 23
<212> TYPE: DNA
<213> ORGANISM: Artificial
<220> FEATURE:
<223> OTHER INFORMATION: primer 16S rDNA

<400> SEQUENCE: 9
ggtatctacg cattccaccg cta                                            23
```

LACCASES AND USES THEREOF

CROSS-REFERENCE TO RELATED APPLICATIONS

This application is the U.S. national stage application of International Patent Application No. PCT/EP2011/069670, filed Nov. 8, 2011, which claims the benefit of U.S. Provisional Patent Application No. 61/411,182, filed Nov. 8, 2010.

The Sequence Listing for this application is labeled "2913730.txt" which was created on Jun. 2, 2013 and is 17 KB. The entire contents of the sequence listing is incorporated herein by reference in its entirety.

FIELD OF THE INVENTION

The present invention relates to novel enzymes and the uses thereof. The invention also relates to methods of producing such enzymes, coding nucleic acid molecules, recombinant cells and methods of modifying biomass from such materials. The invention is particularly suited to degrade biomass and/or to improve biomass degradation. The invention also relates to various applications of the enzymes of the invention for the production of bioenergy (such as bioethanol), as well as in the field of chemistry, paper industry, textile industry and beverage industry.

BACKGROUND OF THE INVENTION

The use of microorganisms to conduct modification of biomass for the production of bioenergy products or metabolites has been proposed in the art. Such process, ideally, would require two major types of activities: (i) a degradation activity, to transform biomass into fermentable sugars and (ii) a fermentation activity, to transform said sugars into bioenergy products or other valuable metabolites. So far, efforts have been directed mainly towards the identification of microorganisms having the ability to catalyze the fermentation step.

A monograph on the production of ethanol through fermentation with microorganisms was published under the title "Ethanol Fermentation Strains" by J. R. Hettenhaus, under the aegis of the United States Department of Energy and the National Renewable Energy Laboratory (Dec. 16, 1998). In this document, which summarizes the contributions made by participants in the study, it is pointed out that:
- only microorganisms similar to *Saccharomyces, Zymomonas* and *E. coli* can be used in existing equipment;
- in the short term, the increased fermentation of xylose and arabinose could be the main objective, it being specified however that it is of little interest to increase the converting efficacy of the other sugars of hexose or oligomer type;
- over the longer term, gains could be achieved regarding higher operating temperatures and combining of the steps of enzyme production, saccharification and hydrolysis.

Current industrial processes only allow the culture and growth of microorganisms for the fermentation and extraction of ethanol at temperatures in the region of 30° C., owing to the fragility of the industrial microorganisms (yeasts) used. They also entail major bioenergy costs to concentrate the ethanol after fermentation, since yeasts currently used for this fermentation cannot withstand ethanol concentrations above 100 g/l. Additionally, the fermentation of yeasts practically only uses C6 sugars, of glucose type.

The conversion of biomass using microorganisms has also been tested (Blumer-Schuette et al., 2008, Extremely thermophilic microorganisms for biomass conversion: status and prospects, Curr Opinion Biotechnol 19, pp. 210-217; Perez et al., 2002, Int Microbiol 5, pp 53-63). However, as reported in Mosier et al. (Bioresource Technology 96 (2005) 673-686), a pre-treatment of lignocellulosic biomass is required to alter the structure of cellulosic biomass to make cellulose more accessible to the enzymes that convert the carbohydrate polymers into fermentable sugars.

The industrial and efficient production of fermentable sugars (e.g., monomeric sugars) from raw (i.e., starch, lignocellulosic) biomass still remains a challenge.

Various approaches have been proposed to exploit biomass, such as thermochemical methods, acid hydrolysis or enzymatic hydrolysis. Sun H et al (Appl Biochem Biotechnol. 2010 February; 160(4):988-1003) discusses the use of enzymes for the degradation of starch. Polizeli M L et al, and Collin T et al (Appl Microbiol Biotechnol. 2005 June; 67(5): 577-591; FEMS Microbiol Rev. 2005 January; 29(1):3-23) review the use of enzymes for the degradation of xylan. Wilson D B et al (Curr Opin Biotechnol. 2009 June; 20(3):295-299) discusses the use of enzymes for the degradation of cellulose for biofuel applications. In the case of lignin, only very few methods have been considered which imply the use of organo-solvents and incineration.

SUMMARY OF THE INVENTION

The present invention discloses the identification and characterization of a laccase from a *Deinococcus* bacterium. Laccases are enzymes having the rare capacity to degrade lignin, the most complex constituent of biomass.

The invention is the first to report the identification and isolation, from *Deinococcus* bacteria, of a functional enzyme involved in lignin processing.

The present invention therefore concerns said enzyme, its manufacture and uses. The invention also relates to nucleic acids encoding the enzyme, vectors, recombinant cells and their uses. The invention further relates to compositions and methods for modifying biomass and/or producing valuable products from biomass or derivatives thereof.

An object of this invention thus relates to a laccase derived from a *Deinococcus* or a related bacterium.

A further object of this invention is an enzyme, wherein said enzyme derives from a *Deinococcus* or a related bacterium and has the ability to degrade or hydrolyze lignin.

A further object of this invention is an enzyme, wherein said enzyme derives from a *Deinococcus* or a related bacterium and is involved in biofuel production.

A further object of this invention is an enzyme, wherein said enzyme derives from a *Deinococcus* or a related bacterium and has the ability to breakdown lignin polymers.

The enzymes of the invention are preferably active at a temperature of 30° C. or more, even more preferably of 40° C. or more.

Furthermore, the enzymes of the invention are preferably active in a range of pH from 3.5 to 9, more preferably in a range of pH from 6 to 9.

Most preferred enzymes of the invention are of *Deinococcus* origin.

A further object of this invention is a polypeptide comprising all or part of the amino acid sequence of SEQ ID NO: 2, 4 or 6.

A further object of this invention is a composition comprising at least one enzyme as defined above. The composition may comprise additional enzymes, preferably active in energetic metabolism. The composition may be used e.g., as a catalyst or starter.

In a particular embodiment, the invention relates to a composition comprising a laccase of the invention and at least one additional enzyme involved in biomass modification, preferably selected from xylanases, amylases, glucosidases, cellulases, pectinases, esterases, feruloyl esterases, acetyl xylan esterases, and glucuronidases.

In another particular embodiment, the invention relates to a composition comprising a laccase of the invention and at least one additional enzyme involved in sugar fermentation, particularly ethanol production by fermentation. Examples of such additional enzymes include acetaldehyde dehydrogenases, alcohol dehydrogenases and pyruvate dehydrogenases.

A further object of the invention is a nucleic acid coding an enzyme as defined above.

A further object of the invention is a vector comprising a nucleic acid as defined above.

The invention also relates to a recombinant cell containing at least one nucleic acid or a vector as defined above, preferably a recombinant bacterium containing at least one nucleic acid or a vector as defined above.

The invention also relates to a *Deinococcus* or a related bacterium which contains at least one nucleic acid or vector as defined above. The invention indeed allows the engineering of *Deinococcus* strains with improved capacity to process lignocellulosic biomass, with the use of *Deinococcus* DNA only.

The invention also relates to an extract of a cell of the invention. Such an extract preferably exhibits an activity of the expressed enzyme.

The invention also relates to the use of an enzyme, nucleic acid, vector, cell or cell extract as defined above for modifying biomass and/or producing metabolites.

The invention also relates to a method for modifying biomass, comprising exposing such biomass to an enzyme, nucleic acid, vector, cell or cell extract as defined above.

The invention also relates to a method for modifying biomass, wherein said biomass further comprises a natural or synthetic mediator.

The invention also relates to a method for increasing biomass modification, the method comprising adding to the biomass an enzyme, nucleic acid, vector, cell or cell extract as defined above. The invention also relates to a method for producing metabolites or bioenergy products, comprising exposing a carbon source to an enzyme, nucleic acid, vector, cell or cell extract as defined above. The invention also relates to a method for producing metabolites or bioenergy products, wherein said carbon source further comprises a natural or synthetic mediator.

The invention also relates to a method of modifying lignin, comprising exposing lignin or a lignin-containing material, to an enzyme, nucleic acid, vector, cell or cell extract as defined above. The invention also relates to a cloth-washing or dish-washing composition, wherein said composition comprises an enzyme, nucleic acid, vector or cell as defined above.

The invention also relates to a method for wood delignification and/or pulp bleaching, comprising exposing a wood pulp or paper to an enzyme, nucleic acid, vector or cell as defined above. The invention also relates to a method for wood delignification and/or pulp bleaching, wherein said wood pulp or paper further comprises a natural or synthetic mediator.

DETAILED DESCRIPTION OF THE INVENTION

The invention relates, generally, to valuable enzymes derived from *Deinococcus* or related bacterial strains, which are involved in energetic metabolism, more preferably in biomass modification. These enzymes, which are preferably active at 30° C., even more preferably at 40° C. or more, and in a range of pH from 3.5 to 9, more preferably in a range of pH from 6 to 9 (e.g. at pH8) can be used as such, alone or in combination(s), to cause or improve enzymatic reactions. These enzymes, or their coding nucleic acids, may also be used to create improved recombinant bacteria which may serve to cause or improve biomass conversion. Such bacteria may combine different enzymatic activities or biological properties.

The present disclosure will be best understood by reference to the following definitions:

"Within the context of the invention, the term "derived from a *Deinococcus* bacterium or related bacterium" in relation to an enzyme indicates that the enzyme has been isolated from such a bacterium, or that the enzyme comprises all or a biologically active part of the amino acid sequence of an enzyme isolated, purified or characterized from such a bacterium. The term "derived from a *Deinococcus* bacterium or related bacterium" further includes any recombinant, synthetic and/or optionally modified enzyme (e.g., modified chemically, enzymatically, physically) synthesized from a nucleic acid or amino acid sequence identified in a *Deinococcus* or a related bacterium.

"*Deinococcus* bacterium" designates any bacterium species of the genus *Deinococcus*. *Deinococcus* bacterium includes, without limitation, *D. cellulolysiticus, D. radiodurans, D. proteolyticus, D. radiopugnans, D. radiophilus, D. grandis, D. indicus, D. frigens, D. saxicola, D. maricopensis, D. marmoris, D. deserti, D. geothermalis, D. murrayi, D. aerius, D. aerolatus, D. aerophilus, D. aetherius, D. alpinitundrae, D. altitudinis, D. apachensis, D. aquaticus, D. aquatilis, D. aquiradiocola, D. aquivivus, D. caeni, D. claudionis, D. ficus, D. gobiensis, D. hohokamensis, D. hopiensis, D. misasensis, D. navajonensis, D. papagonensis, D. peraridilitoris, D. pimensis, D. piscis, D. radiomollis, D. roseus, D. sonorensis, D. wulumuqiensis, D. xibeiensis, D. xinjiangensis, D. yavapaiensis* and *D. yunweiensis*.

A bacterium or a bacterial strain "related" to *Deinococcus* designates a bacterium which (i) contains a 16S rDNA which, upon amplification using primers GTTACCCGGAAT-CACTGGGCGTA (SEQ ID NO: 8) and GGTATCTACG-CATTCCACCGCTA (SEQ ID NO: 9), generates a fragment of about 158 base pairs and/or (ii) resists a UV treatment of 4 mJ/cm$^2$. In a particular embodiment, *Deinococcus*-related bacteria are bacteria having a 16S rDNA molecule which is at least 70%, preferably at least 80% identical in sequence to a *Deinococcus* 16S rDNA sequence.

The term "purified" or "isolated", in relation to an enzyme or nucleic acid, indicates the enzyme or nucleic acid is not in its natural medium or form. The term "isolated" thus includes an enzyme or nucleic acid removed from its original environment, e.g., the natural environment if it is naturally occurring. For instance, an isolated enzyme is typically devoid of at least some proteins or other constituents of the cells to which it is normally associated or with which it is normally admixed or in solution. An isolated enzyme includes said enzyme naturally-produced contained in a cell lysate; the enzyme in a purified or partially purified form, the recombinant enzyme, the enzyme which is expressed or secreted by a bacterium, as well as the enzyme in a heterologous host cell or culture. In relation to a nucleic acid, the term isolated or purified indicates e.g., that the nucleic acid is not in its natural genomic context (e.g., in a vector, as an expression cassette, linked to a promoter, or artificially introduced in a heterologous host cell).

The term "energetic metabolism" designates all biological pathways and reactions that contribute to creating or stocking energy products or metabolites in a cell. These include, without limitation, pathways and reactions such as biomass processing, e.g., the degradation of polymers of biomass into fermentable sugars, and sugar fermentation into valuable metabolites or products. An enzyme involved in biomass processing includes, more preferably, an enzyme that modifies or degrades or hydrolyses materials such as lignin, starch, xylan or cellulose; or an enzyme that contributes to using pyruvate to generate metabolites or energy products in a cell.

The term "biomass" according to the invention typically designates any biological material. In particular, the term biomass includes unprocessed material of biological origin, including vegetal or animal biomass. Examples of biomass include, without limitation, forestry products, including mature trees unsuitable for lumber or paper production, pulp, recycled paper, organic waste, agricultural products, such as grasses, straw, crops and animal manure, and aquatic products, such as algae and seaweed. Examples of biomass include wood or vegetal material derived from numerous types of plants, including miscanthus, hemp, switchgrass, sugarbeet, wheat, barley, corn, rice, soy, canola, rapeseed, sorghum, sugarcane, peanut, cotton, lupine, and a variety of tree species, ranging from eucalyptus to oil palm, poplar, willow. Specific sources of biomass include, without limitation, plant residues, hardwood or softwood stems, cobs, straw, grass, leaves, seeds, paper, etc. (see for instance Sun et al., Bioresource Technology 83 (2002) 1-11). The term biomass also encompasses transformed biomass or secondary biomass, which essentially contains hydrolysed pre-treated biomass products. In a preferred embodiment, biomass according to the invention comprises any lignocellulosic material, for example, lignin, cellulose, hemicelluloses and/or xylan.

"Modifying" a biomass within the context of the present invention includes any modification thereof, including transformation, degradation, hydrolysis, conversion or processing of a biomass. The term "modifying" a biomass typically encompasses any modification of the biomass that results in the production of fermentable sugars, monomeric sugars, metabolites, biofuels and/or chemicals, or any other useful product. Modification also typically encompasses the hydrolysis or modification of biological polymers of the biomass, such as lignin.

The term "fermentable sugar" designates, without limitation, carbohydrates having a basic composition $(CH_2O)_n$. Based on the number of carbons (e.g., 3, 4, 5, or 6), the oligosaccharide is a triose, (i.e., glycerol), tetrose, pentose (i.e., xylose), hexose (i.e., glucose), etc.

Starch refers to a carbohydrate consisting of a large number of glucose units joined together by 1-4 and 1-6 glycosidic bonds. Starch is an energy storage molecule accumulated by many plants and bacteria, and starch molecules arrange themselves in the plant in semi-crystalline granules.

Lignin-Modifying Enzymes

The present invention discloses the isolation and characterization of novel enzymes involved in biomass processing. More particularly, the invention provides novel enzymes which modify (or contribute to the modification of) biomass into fermentable sugars, at temperatures of preferably 30° C. or more, typically between 30 and 90° C., preferably between 30 and 70° C., and in a range of pH from 3.5 to 9, more preferably in a range of pH from 6 to 9, for example at pH8.

The enzymes of the invention catalyze, or contribute to the catalysis of, degradation of lignin into fermentable sugars and represent the first functional enzymes involved in lignin processing isolated from *Deinococcus* bacteria. Because of their activity, structure and physicochemical properties, these enzymes represent novel highly valuable products for use in industrial biomass degradation processes, in treating environmental pollutants, in detoxification, in bioenergy production, in synthetic chemistry, in pulp and paper industry, in textile industry, in washing powders, in beverage industry, as well as in the cosmetic and medical field.

Laccases of the present invention are multi-copper enzymes having the capacity to degrade lignin. The multi-copper enzymes are involved in various biological processes, such as immunity, morphogenesis of organisms, as well as lignification of cell walls. Several enzymes are involved in the degradation of lignin. These can be classified into two functional groups: (i) laccases and (ii) lignin peroxidases and manganese peroxidases. Laccases are responsible for the first and crucial step in the degradation phase, i.e., the breakdown of the long chains of lignin polymers. Furthermore, the laccases of the invention have the capacity to oxidize both phenolic and non-phenolic lignin related compounds. The laccases of the invention may act on a substrate directly or indirectly, e.g., by means of a mediator. Such a mediator is a molecule which can be oxidized by the laccase thus generating a radical which, in turn, oxidizes another substrate. The use of a mediator enables the oxidative transformation of substrates with high redox potentials. Mediators according to the invention may be various laccase natural or synthetic substrates. They may include, e.g., phenols, aniline, 4-hydroxybenzoic acid, ABTS [2,2'-azino-bis-(3-ethylbenzothiazoline-6-sulfonic acid)], 1-hydroxybenzotriazole, 4-hydroxybenzyl alcohol, etc., as described, for instance, in Morozova et al., 2007.

In a particular embodiment, the laccases of the invention exhibit a strong or enhanced activity in the presence of a natural or synthetic mediator.

More particularly, as shown in the experimental part, the enzymes of the invention are active on a broad range of substrates, such as phenols, methoxyphenols, o-diphenols and p-diphenols, aminophenols, polyphenols, polyamines and lignin-related molecules. Enzymes of the present invention preferably comprise all or an active part of the amino acid sequence of SEQ ID NO: 2, 4 or 6 or a functional variant thereof.

The polypeptides of SEQ ID NO: 2 and 4 have been characterized from *Deinococcus cellulolysiticus*, and the polypeptide of SEQ ID NO: 6 has been characterized from *Deinococcus maricopensis*.

A "part" of a polypeptide denotes any fragment of said polypeptide, preferably a fragment comprising at least about 10, 15, 20, 25, 40, 50 or even more preferably 60 contiguous amino acids of said polypeptide.

An "active" part of a polypeptide more specifically designates a part of that polypeptide which confers or exhibits an enzymatic activity of the entire polypeptide. The active part may, for instance, confer substrate specificity or affinity, it may contain the catalytic site, or it may confer pharmacokinetic properties.

"Functional variants" according to the invention retain an activity of the reference polypeptide. They typically also exhibit at least 50% amino acid sequence identity to the reference polypeptide, even more preferably at least 60%, 70%, 80% or 90%. The extent of sequence identity (homology) may be determined using any computer program and associated parameters, including BLAST 2.2.2 or FASTA version 3.0t78, with the default parameters. Preferred functional variants have a level of identity of at least 90% with the reference sequence, most preferably of at least 92, 95, or 97%.

In a preferred embodiment, functional variants comprise at most between 1 to 50, 1 to 40, 1 to 30, 1 to 25, 1 to 20, 1 to 15, 1 to 10, or 1 to 5 modified (e.g., deleted, substituted or inserted) amino acid residues as compared to the reference polypeptide.

Polypeptides according to the invention qualify as functional if they exhibit at least 20%, preferably at least 30% and more preferably at least 50% of an enzymatic activity of the reference polypeptide. Polypeptides may be functional, either by themselves or when fused to or combined with another polypeptide. Also, the polypeptides of the invention may be used to create fusion or chimeric polypeptides having multiple activities. Functional polypeptides are, preferably, polypeptides having the capacity to hydrolyse or modify or breakdown lignin. A further example of a functional test is disclosed in the experimental section.

In a preferred embodiment, enzymes of the present invention are polypeptides comprising an amino acid sequence of SEQ ID NO: 2, 4 or 6 or fragments thereof comprising at least 15 contiguous amino acid residues or functional variants thereof, said fragments or variants having laccase activity.

The invention also relates to a polypeptide comprising all or part of SEQ ID NO: 2, 4 or 6.

Polypeptides of the invention may be produced by recombinant techniques, or they may be isolated or purified from natural sources, when naturally-occurring, or they may be artificially produced. The enzymes may be in soluble form, or on solid phase. In particular, they may be bound to cell membranes or lipid vesicles, or to synthetic supports such as glass, plastic, polymers, filter, membranes, e.g., in the form of beads, columns, plates and the like.

Enzymes of the present invention are polypeptides, which may be naturally-occurring, recombinant and/or synthetic and, optionally modified (e.g., chemically, enzymatically, physically, etc.). The enzymes are preferably in isolated or purified form. The enzymes are advantageously functional at 30° C., or at higher temperatures. Preferred enzymes of the invention may be used at temperatures above 45° C., for instance. In another embodiment, preferred enzymes of the invention are active at a very high temperature, for example, in a temperature range between 60° C. and 90° C., more preferably between 70° C. and 90° C. They are also active under stringent pH (e.g., between 3.5 and 9), preferably in a range of pH from 6 to 9, more preferably in a range from pH7 to pH9, even more preferably at pH8 and in areas closed to pH8. The most preferred enzymes of the invention are active at a high temperature comprised between 70° C. and 90° C. and at an alkaline pH comprised between pH7 and pH9. Such thermostable laccases active at an alkaline pH are particularly efficient in lignin degradation.

Enzymes of the invention may be expressed, derived, secreted, isolated, or purified from a *Deinococcus* or related bacterium. The enzymes may be purified by techniques known per se in the art, and stored under conventional techniques. The polypeptides may be further modified to improve e.g., their stability or activity. They may be used as such, in purified form, either alone or in combinations, to catalyze enzymatic reactions involved in the transformation of raw biomass into fermentable sugars. They may be used to supplement biological processes of transformation of biomass into fermentable sugars. For instance, they may be added into reactors containing microorganisms or enzymes, to supplement the activity. In a preferred embodiment, these enzymes are used to engineer improved microorganisms having novel biological activities. In other specific embodiments, the enzymes of the invention may be used in the production of bioenergy (such as bioethanol), in industrial biomass degradation processes, in bioenergy production, in treating environmental pollutants, in detoxification, in synthetic chemistry, in pulp and paper industry (pulping, paper bleaching), in textile industry (e.g., in stains removal), in washing powders, in beverage industry, (e.g., in brewery, in treating of wines and juices), as well as in the cosmetic and medical field, as described below.

Nucleic Acid

A further object of the invention is a nucleic acid encoding an enzyme or polypeptide as defined above. A further object of the invention is a vector comprising a nucleic acid as defined above.

The term "nucleic acid" designates any type of nucleic acid, such as DNA, RNA, PNA, DNA-like or RNA-like material, which may be of recombinant, artificial and/or synthetic origin, single-stranded or double-stranded, and represent the sense or antisense strand. The term encompasses nucleic acids containing known analogues of natural nucleotides. The term also encompasses nucleic-acid-like structures with synthetic backbones.

A specific example of such nucleic acids is a nucleic acid comprising a sequence of SEQ ID NO: 1, 3 or 5.

SEQ ID NO: 1 comprises a nucleic acid sequence encoding the protein of SEQ ID NO: 2. SEQ ID NO: 3 comprises a nucleic acid sequence encoding the protein of SEQ ID NO: 4. SEQ ID NO: 5 comprises a nucleic acid sequence encoding the protein of SEQ ID NO: 6.

The nucleic acids of the invention can be in isolated or purified form, and made, isolated and/or manipulated by techniques known per se in the art, e.g., cloning and expression of cDNA libraries, amplification, enzymatic synthesis or recombinant technology. The nucleic acids can also be synthesized in vitro by well-known chemical synthesis techniques, as described in, e.g., Belousov (1997) Nucleic Acids Res. 25:3440-3444.

The invention also encompasses nucleic acids which hybridize, under stringent conditions, to a nucleic acid encoding an enzyme as defined above. Preferably, such stringent conditions include incubations of hybridization filters at about 42° C. for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding a polypeptide of the invention, wherein the sequence of said nucleic acids, or a portion of said sequence at least, has been engineered using optimized codon usage.

A specific embodiment of this invention resides in a polynucleotide encoding an enzyme as defined above, comprising the sequence of SEQ ID NO: 1, 3 or 5.

Nucleic acids of this invention may comprise additional nucleotide sequences, such as regulatory regions, i.e., promoters, enhancers, silencers, terminators, and the like that can be used to cause or regulate expression of an enzyme in a selected host cell or system.

A further aspect of this invention resides in a vector, such as an expression, cloning or reporter vector comprising a nucleic acid as defined above. Such vectors may be selected from plasmids, recombinant viruses, phages, episomes, artificial chromosomes, and the like. Many such vectors are commercially available and may be produced according to recombinant techniques well known per se in the art, such as the methods set forth in manuals such as Sambrook et al., *Molecular Cloning* (2d ed. Cold Spring Harbor Press 1989), which is hereby incorporated by reference herein in its entirety. A specific example of such a plasmid is described e.g., in US patent application No. 2003/0175977, which discloses an endogenous plasmid derived from a strain of *D. radiopugnans*, pUE30, which can be used as vector able to replicate autonomously in bacteria of genus *Deinococcus*, and which can be used to construct a shuttle vector also containing a plasmid able to replicate autonomously in *E. coli* and its derivatives, and able to replicate in a bacterium both of genus *Deinococcus* and of *E. coli*.

A further aspect of this invention resides in a host cell transformed or transfected with at least one nucleic acid or a vector as defined above. The nucleic acid (or the vector) may remain extrachromosomal, or become inserted in the genome, e.g., through homologous or heterologous recombination. The host cell may be any cell that can be genetically modified and, preferably, cultivated. The cell can be eukaryotic or prokaryotic, such as a mammalian cell, an insect cell, a plant cell, a yeast, a fungus, a bacterial cell, etc. Typical examples include bacteria (e.g., *E. coli, Deinococcus*, etc). It should be understood that the invention is not limited with respect to any particular cell type, and can be applied to all kinds of cells, following common general knowledge. Transformation may be carried out using techniques known per se in the art, such as lipofection, electroporation, calcium phosphate precipitation, etc.

In yet another embodiment, the present invention includes a recombinant cell that contains at least one vector as defined above. The invention also relates to a recombinant cell containing at least one nucleic acid or a vector as defined above. The invention also relates to a *Deinococcus* bacterium which contains at least one nucleic acid or a vector as defined above. The invention indeed allows the engineering of *Deinococcus* strains with improved capacity to process starch and lignocellulosic biomass, with the use of *Deinococcus* DNA only.

Methods of Use

The present invention provides methods using enzymes of the invention in various industrial, agricultural, chemical, biotechnological and medical areas. Indeed, due to their high catalytic efficiency and broad substrate specificity, laccases of the invention are much more advantageous in comparison with other known chemical and microbial catalysts. The laccases of the invention may be used, for example, in biomass processing, in delignification and pulp bleaching, in biofuel production, in bioremediation, in textile industry, in beverage industry, in pharmaceutics, in organic synthesis, etc. The laccases of the invention may also be used in the presence of natural or synthetic mediators.

Biomass Modification and Bioenergy Production

The laccases of the present invention can be used in methods for modification of a biomass or any lignocellulosic material comprising cellulose, hemicelluloses and/or lignin. In a particular embodiment, the biomass is a lignin-containing material of vegetal origin. The enzymes of the invention can be applied, for example, for the conversion of a biomass into fermentable sugars and/or monomeric sugars and/or for the production of metabolites and/or energy products (e.g., biofuels) from a biomass.

The invention also relates to the use of an enzyme, nucleic acid, vector or cell as defined above, or a combination thereof, for modifying biomass and/or producing metabolites or energy products.

The invention also relates to a method for modifying biomass, comprising exposing such biomass to an enzyme, nucleic acid, vector or cell as defined above, or to a combination thereof. The invention also relates to a method for increasing biomass modification, the method comprising adding to the biomass an enzyme, nucleic acid, vector or cell as defined above, or a combination thereof.

The invention also relates to a method for producing metabolites or bioenergy products, comprising exposing a carbon source to an enzyme, nucleic acid, vector or cell as defined above, or a combination thereof. The method may further comprise a step of isolating or recovering the metabolite or product. Examples of metabolites include, without limitation, organic acids and alcohols such as, preferably, formate, lactate, acetate, succinate, fumarate, pyruvate, propanol, mannitol and arabitol. Examples of energy products include biofuels such as, without limitation, ethanol, butanol or methanol. A particular object of the invention concerns a method for producing a biofuel (for example, bioethanol, biomethanol, biopropanol, biobutanol, etc.), comprising exposing a carbon source, e.g., a biomass or constituents thereof and/or a fermentable sugar, to an enzyme, nucleic acid, vector or cell as defined above, or a combination thereof, and recovering biofuel produced.

The invention also relates to a method of modifying lignin comprising exposing lignin, or a lignin-containing material, to an enzyme, nucleic acid, vector or cell as defined above, or a combination thereof. More particularly, the invention can be used to degrade or hydrolyse lignin.

More generally the enzymes of the invention can also be used to engineer microorganisms having the capacity to use cheaper carbon source. Such microorganisms may thus be used to produce any product of interest (e.g., proteins, RNAs, metabolites, etc) at lower cost and/or improved levels. In this respect, the invention also relates to a method for producing a recombinant protein, comprising expressing said protein in a recombinant microorganism encoding at least one enzyme as defined above, or a combination thereof, and recovering the protein produced. Examples of such recombinant proteins include pharmaceutical proteins, or industrial enzymes such as for instance a lipase.

The method can be carried out in any suitable condition or environment allowing modification of the biomass to produce bioenergy products or metabolites. In this regard, the method can be performed in a reactor, in a fermentor, outdoor, in the presence of suitable nutrients or additives, if needed. The method is typically conducted at a temperature above 30° C., and in the presence of suitable substrates.

Bioremediation

The invention also provides methods for bioremediation of contaminating pollutants by using a laccase of the invention. The laccases of the invention may indeed be used to degrade numerous undesirable substances such as contaminants, by-products and toxic compounds present in wastes from several industrial processes. The laccases can be used, for example, for the removal of toxic compounds through oxidative enzymatic coupling of the contaminants, leading to insoluble complex structures. In particular, they can be used for oxidizing phenolic compounds present in wastes from petroleum refining, coal conversion or from production of organic chemicals (e.g., plastic wastes having olefin units).

The laccases of the invention can be also used to oxidize toxic organic pollutants such as xenobiotics, chlorophenols or polycyclic aromatic hydrocarbons (PAHs), etc. The role of laccases in the degradation of PAHs is particularly important since PAHs are highly toxic, carcinogenic, mutagenic and recalcitrant environmental contaminants that have tendency to bio-accumulate.

Furthermore, the laccases of the invention can also be used to reduce the concentration of synthetic heterocyclic compounds, e.g., organic pesticides in the soil. The laccases can also be used to eliminate or reduce odor emitted from garbage disposal sites, livestock farms or pulp mills. They can also be used to decolorize dye house effluents or waste waters from olive oil mills and pulp mills by removing coloured phenolic compounds.

Chemical Synthesis

The invention also provides methods for making numerous organic compounds by using a laccase of the invention as a biocatalyst in organic synthesis.

Polymerizing activity of the laccase can be exploited in various polymer synthesis. Thus, according to the invention, the laccase can be used to synthesize many functional organic compounds including polymers with specific mechanical/electrical/optical properties, textile dyes, cosmetic pigments, flavor agents and pesticides. For instance, by polymerizing natural phenols with a laccase of the invention, new cosmetic pigments or hair dyeing materials can be developed. Laccases can also be used in deodorants, toothpastes, mouthwashes or detergents.

In a particular embodiment, a laccase of the invention is used in hemi-synthesis.

In green chemistry synthesis, a laccase of the invention may be used, for example, to synthesize safe, environment-benign solvents and nonhazardous oxidizing agents.

Medical Applications

Laccases can also be used to synthesize products of pharmaceutical importance such as anti-cancer drugs. The examples of application of laccases of the invention for synthesis of anticancer drugs include, for example, the oxidative coupling of katarantine and vindoline to yield vinblastine, which is especially useful in treating leukemia. Another anti-cancer drug that can be synthesized using a laccase of the invention is actinocin.

The laccases of the invention may also be used in the production of other novel pharmaceutical compounds exhibiting, for example, antibiotic, antiviral, anti-inflammatory or antioxidant properties.

Pulp and Paper Industry

Other methods involving the use of a laccase of the invention comprise methods of producing a paper-making pulp in paper industry. In particular, the invention provides methods of pulping and methods of repulping, by using a laccase of the invention.

Wood pulp contains three main components, namely cellulose fibers, which are desired for papermaking, as well as lignin and hemicellulose. The aim of pulping is to break down the bulk structure of the fiber source into the constituent fiber.

In a particular embodiment, a method of the invention allows separation and degradation of lignin in wood pulp by using a laccase of the invention. The treatment of wood pulp with a laccase of the invention may, for example, provide milder and cleaner strategies of wood delignification that respect the integrity of cellulose. Furthermore, such an oxygen delignification method with a laccase, can be used to replace polluting conventional chlorine-based methods.

Repulping methods according to the invention comprise methods of producing or recycling lignocellulosic materials (such as pulp, paper or cardboard), using a laccase of the invention. The invention also provides methods of deinking and decolorizing a printed paper or a recycled paper pulp.

The present invention also provides methods of pulp or pulp-kraft bleaching which may result in higher pulp yields and energy saving.

Textile Industry

The invention also provides methods of treating fabrics and textiles using a laccase of the invention. The enzymes can be applied during or after the weaving of textiles, or during the desizing stage or during additional fabric processing steps.

In an embodiment, a laccase is used to improve the whiteness in conventional bleaching of cotton. In a particular embodiment, a laccase is used to bleach indigo-dyed denim fabrics to lighter shades. In another particular embodiment, a laccase can be used for anti-shrink treatment of wool.

Washing Powders

In other particular embodiments, a laccase of the invention is used for cleansing, for instance, in a detergent composition, e.g., in dish-washing and in cloth-washing. In a particular embodiment, a laccase of the invention is used for stain removal, for example for removal of tea or coffee stains.

Beverages

Particularly important applications of laccases concern the stabilization of various types of beverages such as fruit juices, beer, wines, etc. In particular, a laccase is used for polyphenol elimination in wines, which must be selective to avoid an undesirable alteration in the wine organoleptic characteristics. Laccases are also used to improve storage life of beverages such as beer. Enzymatic treatment with a laccase can also be performed in order to reinforce the color of tea-based products, in order to form gels for food ingredients, or to remove phenolic browning products from food products.

A vast amount of industrial applications for laccases from certain fungi and bacteria (other than *Deinococcus*), have already been proposed (Mustafa et al., 2005; Bajpai et al., 2006; Witayakran, 2008; Osma et al, 2010). All previously described laccase applications are transposable to methods of use of laccases according to the invention.

The present invention relates to the use of a laccase, nucleic acid, vector or cell as defined in the present application, or a combination thereof, for all the above applications.

As described in the present application, the laccase of the invention may be used in numerous biotechnological processes such as the detoxification of industrial effluents, for example from the paper and pulp, textile and petrochemical industries, use as a tool for medical diagnostics and as a bioremediation agent to clean up herbicides, pesticides and certain explosives in sol. The laccase of the invention is also used as cleaning agent for certain water purification systems, as catalyst for the manufacture of anti-cancer drugs and even as ingredient in cosmetics. Also, its capacity to remove xenobiotic substances and produce polymeric products makes it an extremely interesting and useful tool for bioremediation purposes.

Because of their activity, structure and physicochemical properties, the laccases of the invention represent novel and highly valuable products for use in various industrial, agricultural, chemical, biotechnological and medical areas. Such a laccase enzyme, derived from *Deinococcus* or related bacterial strain, exhibits a higher catalytic activity compared to activity of other conventional enzymes applied by a skilled person in biomass degradation processes, in treating environmental pollutants, in detoxification, in bioenergy production, in synthetic chemistry, in pulp and paper industry, in textile industry, in washing powders, in beverage industry, as well as in the cosmetic and medical field.

The enzyme of the invention may be used either alone or in combination with other enzymes. For example, the enzyme of the invention may be used in combination with one or more additional enzyme(s) selected from xylanases, amylases, glucosidases, cellulases, pectinases, esterases, feruloyl esterases, acetyl xylan esterases, glucuronidases, acetaldehyde dehydrogenases, alcohol dehydrogenases and pyruvate dehydrogenases. The compositions containing the laccase of the invention with at least one additional enzyme can be used for all the uses, methods and applications described above.

When used in combination, the enzymes may be combined simultaneously or sequentially. For instance, two or more enzymes may be combined in a composition, and the composition can be added to biomass or a carbon source, or a reactor, as mentioned above. Alternatively, two or more enzymes may be added sequentially to said biomass, carbon source or reactor, to provide a combined enzymatic activity to the reaction. Similarly, nucleic acids, vectors or cells coding or expressing a combination of enzymes can be used. Also, instead of whole cells, an enzymatically active extract thereof may be used, such as a lysate or supernatant.

Depending on the conditions, the biomass or substrate can be contacted with a product of the invention alone or in combination with other enzymes or microorganisms. It should be understood that the precise amounts of enzyme or bacterium used initially in order to efficiently transform biomass into substantial bioenergy products or metabolites can be adjusted by the skilled artisan depending on the type of bacterium, the type of biomass, and the culture conditions.

In a particular embodiment, the method of the invention is performed in a reactor of conversion of biomass. By "reactor" is meant a conventional fermentation tank or any apparatus or system for biomass conversion, typically selected from bioreactors, biofilters, rotary biological contactors, and other gaseous and/or liquid phase bioreactors. The apparatus which can be used according to the invention can be used continuously or in batch loads.

In the reactor, to implement the method of the invention, at least one enzyme, bacterium or bacterial extract of the invention is used, whilst said reactor is arranged and supplied so that physicochemical conditions are set up and maintained therein so that said enzyme or bacterium is operational.

Depending on the bacterium used, the method may be conducted under aerobiosis, anaerobiosis or microaerobiosis.

Co-Cultures

A further aspect of the invention resides in microorganism co-cultures having improved properties. More specifically, the invention relates to co-cultures using *Deinococcus* bacteria, which co-cultures have improved enzymatic activities (i.e., laccase activities) or physico-chemical properties.

In a particular embodiment, the invention relates to a co-culture of at least two distinct microorganisms, wherein at least one of said microorganisms is a *Deinococcus* bacterium and at least one of said microorganisms is a prokaryotic or eukaryotic cell, wherein said at least two microorganisms are symbiotic to each other, and wherein said at least one *Deinococcus* bacterium exhibits a laccase activity according to the invention.

The prokaryotic or eukaryotic cell may be selected, e.g., from bacteria, yeasts, plant cells, fungi, and mammalian cells. Examples of yeasts include, without limitation, *Saccharomyces, Kluyveromyces, Schizosaccharomyces, Pichia*, etc. Examples of bacteria include *Deinococcus* bacteria, *Bacillus* sp., *E. Coli, Clostridium* sp., etc. Two microorganisms are considered symbiotic to each other when both require the other for its survival and growth. Co cultures of the invention may comprise more than 2 distinct microorganisms, such as 3 or 4. Also, co-cultures may be simultaneous or sequential, preferably simultaneous.

In this regard, a specific object of the invention is a culture of at least two distinct microorganisms, wherein at least one of said microorganisms is a *Deinococcus* bacterium and at least one of said microorganisms is a yeast, and wherein said at least one *Deinococcus* bacterium exhibits a laccase activity according to the invention.

These co-cultures offer improved range of enzymatic activities and represent valuable products for industrial processes.

Further aspects and advantages of the invention will be disclosed in the following examples, which illustrate the invention.

EXAMPLES

Materials and Methods

Selection Tests and Culture Media Composition
167 Thermus medium

| | |
|---|---|
| Tryptone | 1 g |
| Yeast extract | 1 g |
| Agar | 28 g |
| Nitrilotriacetic acid | 100 mg |
| $CaSO_4 \times 2H_2O$ | 40 mg |
| $MgCl_2 \times 6H_2O$ | 200 mg |
| 0.01M Fe citrate | 0.5 ml |
| Solution of trace elements (see below) | 0.5 ml |
| Phosphate buffer (see below) | 100 ml |
| $H_2O$ | 900 ml |

Adjust to pH 7.2 with NaOH, autoclave at 121° C. for 15 min. autoclave the phosphate buffer separately and add to the medium Phosphate Buffer

| | |
|---|---|
| $KH_2PO_4$ | 5.44 g |
| $Na_2HPO_4 \times 12H_2O$ | 43 g |
| $H_2O$ | 1000 ml |

Adjust to pH 7.2

Composition of Minimum Medium

MOPS buffer 1× (ph7) containing: acid MOPS buffer 40 mM, $NH_4Cl$ 20 mM, KOH 10 mM, NaOH 10 mM, $CaCl_2$ 0.5 µM, $Na_2SO_4$ 0.276 mM, $MgCl_2$ 0.528 mM.

A solution of micronutriments (pH5): $(NH_4)_6(MO_7)_{24}$ 3 nM, $H_3BO_3$ 400 nM, $CoCl_2$ 30 nM, $CuSO_4$ 10, nM, $MnCl_2$ 250 nM, $ZnSO_4$ 10 nM.

Solution of vitamins, pH4.0, (1 µg/l each): D-biotin, niacin, pyridoxal-HCl, thiamin-HCl, vitamin B12

Source of phosphate: $K_2HPO_4$ 5.7 mM $FeCl_3$ 20 µM (prepared in a solution of sodium citrate then filtered).

Example 1

Identification of Enzymes with Laccase Activity

*Deinococcus* sp were inoculated on MOPS buffer solution at pH7 and filtered: acid MOPS buffer 40 mM (Sigma, France), $NH_4Cl$ 20 mM, KOH 10 mM, NaOH 10 mM, $CaCl_2$ 0.5 µM, $Na_2SO_4$ 0.276 mM, $MgCl_2$ 0.528 mM), a solution of micronutriments at pH5 $((NH_4)_6(MO_7)_{24}$ 3 nM, $H_3BO_3$ 400 nM, $CoCl_2$ 30 nM, $CuSO_4$ 10 nM, $MnCl_2$ 250 nM, $ZnSO_4$ 10 nM), a solution of vitamins at pH4 (1 µg/L of D-biotin, niacin, pyridoxal-HCl, thiamin-HCl and vitamin B12), a solution of $K_2HPO_4$ at 5.7 mM as well as a solution of $FeCl_3$ at 20 µM in $NaH_2(C_3H_5O(COO)_3)$ and glucose 111 mM.

The bacteria were grown at 45° C. or 30° C. during seven days. Genomic DNA was extracted, the genes coding for putative laccases were amplified by PCR and then analysed. Laccase activity from culture supernatant and from cellular extract was tested in presence of 2,6 dimethoxyphenol (2,6 DMP), ABTS or Syringaldazine.

Two enzymes having laccase activity have been characterized from *Deinococcus* cellulolysiticus DRH46 (namely laccase 1, laccase 2), and one enzyme having laccase activity has been characterized from *Deinococcus* maricopensis DSM 21211 (i.e., laccase 3). The amino acid sequences of laccase 1, laccase 2 and laccase 3 are represented in SEQ ID NO: 2, 4 and 6, respectively.

The coding nucleic acid sequences have also been isolated, and are represented in SEQ ID NO: 1, 3 and 5, respectively.

These nucleic acids have been cloned into the pET-DEST42 expression vector and recombinant bacteria containing said vector have been produced and maintained.

Example 2

Production of Recombinant Enzymes

As mentioned in Example 1, nucleic acids encoding the laccase 1, 2 and 3 enzymes comprising the amino acid sequence of SEQ ID NO: 2, 4 or 6 respectively, were cloned into the pETDEST42 vector according to conventional recombinant techniques. In each vector, the cloned nucleic acid was cloned in frame with a 6(His) tag (SEQ ID NO: 7), to facilitate purification of the recombinant protein.

*E. coli* cells harboring the recombinant nucleic acid are prepared and grown in 4 liters of LB medium. Induction of the enzyme production is performed overnight in the presence of 1 mM IPTG and 2 mM of $Cu_2SO_4$. After centrifugation of the culture, cells are suspended in 50 mM Phosphate buffer pH 7.5, 300 mM NaCl, 5% imidazole, 1 mg/ml Lysozyme and disrupted by sonication. Cell debris are removed by centrifugation and the supernatant is collected and applied to a His-Trap affinity chromatography column (HisTrap™ HP column).

Fractions containing the recombinant polypeptide of SEQ ID NO: 2, 4 or 6 are eluted with buffer containing 300 mM imidazole, 300 mM NaCl, 50 mM phosphate buffer pH7.5 and subsequently desalted against 50 mM pH7.5 phosphate buffer 50 mM NaCl, to purify the protein.

Example 3

Activity of the Recombinant Laccases of SEQ ID NO: 2 and 4

3.1. *E. coli* harboring a recombinant nucleic acid encoding a laccase derived from *Deinococcus* DRH-46 (i.e., Laccase 1 or Laccase 2), cloned into the pET-DEST42 vector, were grown in the presence or absence of 1 mM IPTG in LB medium containing 2 mM of $Cu_2SO_4$.

3.2 Laccase Assay

Standard assays for laccase activity were performed at the temperature range from 30° C. to 90° C. by measurement of enzymatic oxidation of substrates at appropriate wavelength. The reaction was performed in presence of a substrate concentration range, 0.05 mg/mL of purified enzyme and 1 mM prepared in 0.1M citrate-phosphate buffer pH8.

Standard assays were performed using the following substrates: 2,6 DMP, 4-methyl DMP, synapic acid, syringic acid, guaiacol, ABTS, paraphenylenediamine and ferulic acid.

Principle:

2,6 DMP+$O_2$+enzyme→Oxidized 2,6 DMP+$2H_2O$ 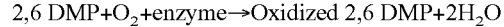

The assay is performed at T=45° C. and 60° C., pH=8. The absorbance was measured at $A_{470\ nm}$ and the measure was carried out using Continuous Spectrophotometric Rate Determination.

Reagents:
A. 100 mM Citrate Phosphate Buffer, pH 8 at 45° C. and 60° C.
B. 30 mM 2,6-dimethoxyphenol solution
C. Laccase Enzyme Solution (2 mg/mL)

Protocol:

Reagent A (185 μl) was mixed with Reagent B (10 μl). The mixture was equilibrated to 45° C. or 60° C. The absorbance at 470 nm was monitored until constant, using a suitably thermoregulated spectrophotometer. Then Reagent C (5 μl) was added and the increase in $A_{470\ nm}$ was recorded for 30 minutes. The $\Delta A_{470\ nm}$/minute was obtained using the maximum linear rate for the Test, Control and Blank, Blank being mixture without enzyme and Control being mixture with laccase from *Trametes versicolor* (*T. versicolor*, commercial enzyme) replacing Laccase enzyme solution (Reagent C).

Other substrates, different from 2,6 DMP such as 4-methyl DMP, synapic acid, syringic acid, guaiacol, ABTS, paraphenylenediamine and ferulic acid have also been tested at optimal concentration for each substrate (as shown in Tables 1A and 1B).

One unit of enzyme activity is defined as amount of enzyme required to oxidize 1 μmol of 2,6 DMP per min using an extinction coefficient $\epsilon_{470\ nm}$ 14.8 $mM^{-1}$. $cm^{-1}$. This definition has to be applied with appropriate extinction coefficient value for other substrates, in particular a phenolic substrate (e.g. 4-methyl DMP, synapic acid, syringic acid, guaiacol, ABTS, paraphenylenediamine, ferulic acid).

Results:

The results for Laccase 1 (SEQ ID NO: 2) and Laccase 2 (SEQ ID NO: 4) activity are shown respectively in Table 1A and Table 1B below.

TABLE 1A

Laccase 1 activity

| Substrates | Activity | Km (mM) | T° C. | Opt. pH | T. versicolor |
|---|---|---|---|---|---|
| 2,6 DMP | + | 0.798 +/− 0.035 | 60° C. | 8 | − |
| 4 methyl DMP | + | | 60° C. | 8 | |
| Syringic acid | + | | 60° C. | 8 | |
| Guaiacol | + | 3.046 +/− 0.183 | 60° C. | 8 | − |
| ABTS | + | | 60° C. | 8 | +/− |
| Ferulic acid | + | | 60° C. | 8 | − |
| Paraphenylene-diamine | + | | 45° C. | 8 | + |
| Synapic acid | + | | 45° C. | 8 | − |

Table 1A shows that the recombinant enzyme of SEQ ID NO: 2, exhibits, in the tested conditions, a laccase activity, thus confirming that the laccase 1 recombinant enzyme is fully active. Interestingly, the laccase 1 activity was found on several different substrates.

TABLE 1B

Laccase 2 activity

| Substrates | Activity | Km (mM) | T° C. | Opt. pH | T. versicolor |
|---|---|---|---|---|---|
| 2,6 DMP | + | 0.992 +/− 0.141 | 60° C. | 8 | − |
| 4 methyl DMP | + | | 60° C. | 8 | |
| Syringic acid | + | | 60° C. | 8 | |
| Guaiacol | + | 5.074 +/− 0.343 | 60° C. | 8 | − |
| ABTS | + | | 60° C. | 8 | + |
| Ferulic acid | + | | 60° C. | 8 | − |
| Paraphenylene-diamine | + | | 45° C. | 8 | +/− |
| Synapic acid | + | | 45° C. | 8 | − |

Table 1B shows that the recombinant enzyme of SEQ ID NO: 4, exhibits, in the tested conditions, a laccase activity, thus confirming that the laccase 2 recombinant enzyme is fully active. Interestingly, the laccase 2 activity was confirmed on several different substrates.

3.3 Temperature and pH Optimum

In another series of experiments, the laccase activity according to the invention, was also tested in different conditions of temperature and pH using various substrates.

Results:
Optimal temperature found for Laccase 1 with 2,6 Dimethoxyphenol (2,6 DMP) as substrate was 90° C.
Optimal temperature found for Laccase 2 with 2,6 DMP as substrate was 70° C.
Optimal pH found for Laccase 1 with 2,6 DMP as substrate was pH 8.
Optimal pH found for Laccase 2 with 2,6 DMP as substrate was pH 8.

In conclusion, laccases of the invention have unique features: they are thermostable at a high temperature and active at basic pH (such as pH 8).

REFERENCES

Mustafa R., Muniglia L., Rovel B., Girardin M. (2005). "Phenolic colorants obtained by enzymatic synthesis using a fungal laccase in a hydro-organic biphasic system". Food Research International 38: 995-1000.

Bajpai P., Anand A., Bajpai P. K. (2006). "Bleaching with lignin-oxidizing enzymes". Biotechnol. Annu. Rev. 12: 349-78.

Witayakran S. (2008). "Laccase in organic synthesis and its applications". Georgie Institute of Technology, School of Chemistry and Biochemistry.

Osma J. F., Toca-Herrera J. L., Rodriguez-Couto S. (2010). "Uses of laccases in the food industry". Enzyme Research, Article ID 918761, 8 pages.

Morozova O. V., Shumakovich G. P., Shleev S. V. and Yaropolov (2007). "Laccase-Mediator Systems and their applications: a review". Applied Biochemistry and microbiology 43, n° 5, 523-535.

The invention claimed is:

1. A heterologous recombinant host cell transformed or transfected with a nucleic acid encoding a laccase wherein said laccase comprises all or a biologically active part of the amino acid sequence of SEQ ID NO: 2 or 4.

2. The host cell of claim 1, wherein said laccase is active at a temperature of 30° C. or more and/or which is active in a range of pH from 3.5 to 9.

3. The host cell of claim 1, wherein said laccase catalyzes biomass modification.

4. The host cell of claim 3, wherein said laccase catalyzes lignin degradation or hydrolysis.

5. The host cell of claim 1, wherein said laccase comprises the amino acid sequence of SEQ ID NO: 2.

6. An isolated nucleic acid encoding a laccase wherein said laccase comprises all or a biologically active part of the amino acid sequence of SEQ ID NO: 2 or 4 linked to a heterologous promoter.

7. A vector comprising a nucleic acid of claim 6.

8. The host cell of claim 1, which is a *Deinococcus* or a related bacterium.

9. A method for modifying biomass, comprising exposing such biomass to a polypeptide host cell of claim 1.

10. A method for producing metabolites or bioenergy products, comprising exposing a carbon source to a laccase host cell of claim 1.

11. A method for wood delignification and/or pulp bleaching, comprising exposing a wood pulp or paper to a host cell of claim 1.

12. The host cell according to claim 1, wherein said nucleic acid is linked to a heterologous promoter.

13. The host cell of claim 1, wherein said laccase comprises the amino acid sequence of SEQ ID NO: 2.

14. A cell extract of the host cell according to claim 1, said extract exhibiting a laccase activity.

15. A method for modifying biomass, comprising exposing such biomass to a cell extract of claim 14.

16. A method for producing metabolites or bioenergy products, comprising exposing a carbon source to a cell extract of claim 14.

17. A method for wood delignification and/or pulp bleaching, comprising exposing a wood pulp or paper to a cell extract of claim 14.

18. A recombinant cell transformed or transfected with a nucleic acid encoding a laccase, wherein said laccase comprises all or a biologically active part of the amino acid sequence of SEQ ID NO: 2 or 4 and wherein said nucleic acid is linked to a heterologous promoter.

* * * * *

UNITED STATES PATENT AND TRADEMARK OFFICE
CERTIFICATE OF CORRECTION

PATENT NO. : 9,068,161 B2  
APPLICATION NO. : 13/884103  
DATED : June 30, 2015  
INVENTOR(S) : Jean-Paul Leonetti, Jean-Michel Claverie and Nicolas Chabot Page 1 of 1

It is certified that error appears in the above-identified patent and that said Letters Patent is hereby corrected as shown below:

In the claims

Column 29,
Line 48, "to a polypeptide host" should read --to a host--.
Line 50, "to a laccase host" should read --to a host--.

Column 30,
Line 33, "SEQ ID NO: 2." should read --SEQ ID NO: 4.--.

Signed and Sealed this
Twenty-second Day of March, 2016

Michelle K. Lee
*Director of the United States Patent and Trademark Office*